United States Patent [19]
Torii et al.

[11] Patent Number: 6,004,588
[45] Date of Patent: Dec. 21, 1999

[54] FAR-INFRARED RADIATION MATERIAL

[76] Inventors: Kazuyuki Torii, 1-29, Kitahama 3-chome, Beppu-shi, Oita; Kozo Niwa, 4-4, Asahimachi, Tosashimizu-shi, Kouchi, both of Japan

[21] Appl. No.: 08/770,254

[22] Filed: Dec. 20, 1996

[30] Foreign Application Priority Data

Dec. 25, 1995 [JP] Japan ................................. 7-337559

[51] Int. Cl.⁶ .................................................. A61K 33/06
[52] U.S. Cl. ......................... 424/682; 424/600; 424/646; 424/724
[58] Field of Search .................................. 424/600, 646, 424/682, 724

[56] References Cited

FOREIGN PATENT DOCUMENTS

| 1 094 992 | of 0000 | China . |
| 0 347 197 | 12/1989 | European Pat. Off. . |
| 02 062 812 | of 0000 | Japan . |
| 08 059 488 | of 0000 | Japan . |
| 010281018 | 11/1989 | Japan . |
| 010289423 | 11/1989 | Japan . |
| 03 112 849 | 5/1991 | Japan . |
| 08175863 | 7/1996 | Japan . |

OTHER PUBLICATIONS

Niwa Y., Iizawa O., Ishimoto K., Jiang X., Kanoh T., "Electromagnetic Wave Emitting Products and 'Kikoh' Potentiate Human Leukocyte Functions" *International Journal of Biometeorology*, 37(3);133–138.

Primary Examiner—Jean C. Witz
Attorney, Agent, or Firm—McCormick, Paulding & Huber

[57] ABSTRACT

Provided are a far-infrared radiation material and a medicine and a food derived therefrom. The far-infrared radiation material is obtained by steps comprising pulverizing a stone (SGES) having been absorbing solar energy for a geologically long time, emitting far-infrared radiation of the wavelength 4–14 $\mu$m and comprising at least about 28% of Si, about 10% of Al, about 6% of K and about 4% of Fe, and forming the pulverized stone into spheres. This material can be used as sand for a sand bath. Also ultrafine powder obtained by pulverizing the SGES and grinding the pulverized SGES can be used as a medicine or a food.

4 Claims, 1 Drawing Sheet

FAR-INFRARED RADIATION MATERIAL

BACKGROUND OF THE INVENTION

1. Field of the Invention

The present invention relates generally to a far-infrared radiation material and a medicine and a food derived therefrom. In particular, the far-infrared radiation material is one that is remarkably effective for activating normal cells, for inhibiting the lipid peroxide production, and for inhibiting the proliferation of leukemia and transplanted cancer cells.

2. Related Art Statement

Stones such as granite, platinum, tourmaline and so on have been known to emit far-infrared radiation of the wavelength 4–14 μm.

The far-infrared radiation emitted from these stones dissociates water clusters into the molecules. Thus impurities inside water clusters can be removed by applying the radiation, whereby the water is purified. For example, water contaminated with such gases as sulfurous acid gas, hydrochloric acid gas, carbonic acid gas, and so on, which lie inside the water clusters, is purified by applying the radiation since it cleaves the clusters, and thus the gases are released therefrom. Also for the case of contamination of water with such heavy metals as mercury, cadmium, and so on, the application of the radiation causes the dissociation of the clusters which include the metals inside, and consequently these metals precipitate. Then by removing the precipitates from the water, the water is purified.

The far-infrared radiation having the wavelength 4–14 μm have been known as "growth ray", which is energy necessary for raising animals and plants.

Recently, researches by the present inventors have shown that the above-described radiation activates animal and plant cells as well as inhibits the lipid peroxide production which is considered to be one of factors causing such diseases as rheumatoid arthritis, thrombophlebitis, progressive systemic scleroderma, Buerger's disease, Raynaud's disease, intractable dermatoulcer, and the like. It has also been proved that the application of such radiation to a human body promotes the circulation of blood, and is widely useful in preventing paralysis and cardiac infarction as well as in curing a topic dermatitis. Furthermore, the present inventors have proved that the radiation inhibits even the activity of cancer cells (See *Igaku to Seibutsugaku*, Vol. 123: pp. 113–118, 1991, *Ensho*, Vol. 11: pp. 135–141, 1991, *Ensho*, Vol. 12: pp. 63–69, 1992, *Int. J. Biometeorol.*, Vol. 37: pp. 133–138, 1993).

However, the far-infrared radiation emitted from these known stones, granite and tourmaline, does not show the remarkable effect to all the following actions: the activation of normal cells, the inhibition of the lipid peroxide production, and the inhibition of the proliferation of leukemia and transplanted cancer cells.

The present inventors have utilized a particular stone, SOES (super growth-ray emitting stone), as described below, to make experiments relating to the effects of the far-infrared radiation emitted therefrom. The radiation from SGES has been applied to cancer cells transplanted to a mouse, to human white blood and leukemia cells, and to lipid peroxides. Compared with the known stones, SGES has been found to be remarkably effective, whereby the present invention has been accomplished.

SUMMARY OF THE INVENTION

An object of the present invention is to provide a use of the far-infrared radiation material as sand for a sand bath obtained by pulverizing SGES and forming the pulverized SGES into spheres.

Another object of the present invention is to provide a use of the far-infrared radiation material as a medicine or a food obtained by pulverizing SGES and grinding the pulverized SGES into ultrafine powder.

The far-infrared radiation material of the present invention can be obtained by processing SGES according to the following method.

SGES as a starting material of the present invention is a stone having been absorbing solar energy for a geologically long time, which emits far-infrared radiation of the wavelength 4–14 μm, the stone comprising at least about 28% of Si, about 10% of Al, about 6% of K and about 4% of Fe. In particular, preferred is one mined from the Sobo Mountains in Oita, Japan.

In order to increase the amount of the far-infrared radiation emitted from the surface of the stone, the surface area to the constant weight should be increased; that is, the SGES is pulverized. More specifically, the SGES is crushed by a crusher and then is pulverized by a jet mill.

The pulverized SGES is now formed into spheres. More specifically, the pulverized SGES is sintered at 1,100–1,150° C. for 15–25 hours so as to be formed into spheres of the diameter 3–5 mm (we call these spheres "ceramic balls" hereinafter).

For the case of a use of the far-infrared radiation material as sand of a sand bath, the amount of the far-infrared radiation is increased as several ten times much as that at room temperature, and thus the SGES ceramic balls are warmed. More specifically, the SGES ceramic balls heated at 50–70° C. are laid in a bath tub, and then hot water at the temperature a little higher than body temperature or 50–53° C. is poured into the tub with the ceramic balls. When the hot ceramic balls are cooled to the temperature whereat a person can bear or 45–46° C., the person is ready to take a sand bath for 15–20 minutes.

The far-infrared radiation material of the present invention can be used as a medicine. More specifically, the SGES pulverized by the above-described method is further let collide with each other by a jet mill so as to be ground into ultrafine powder of the diameter not more than 1 μm. A medicine including the SGES ultrafine powder is applied, for example, internally so that a person weighing about 60 kg can take the powder of 0.2–0.4 g per day.

Furthermore, since the SGES ultrafine powder is free from side effects, it can be taken as a health food for maintaining and promoting a person's health. For example, the SGES ultrafine powder can be added when cooking. Also soft drinks with the SGES ultrafine powder can be served.

Other features and advantages of the present invention will become readily apparent from the following written description and drawings.

DETAILED DESCRIPTION OF THE PREFERRED EMBODIMENT

Figure 1:
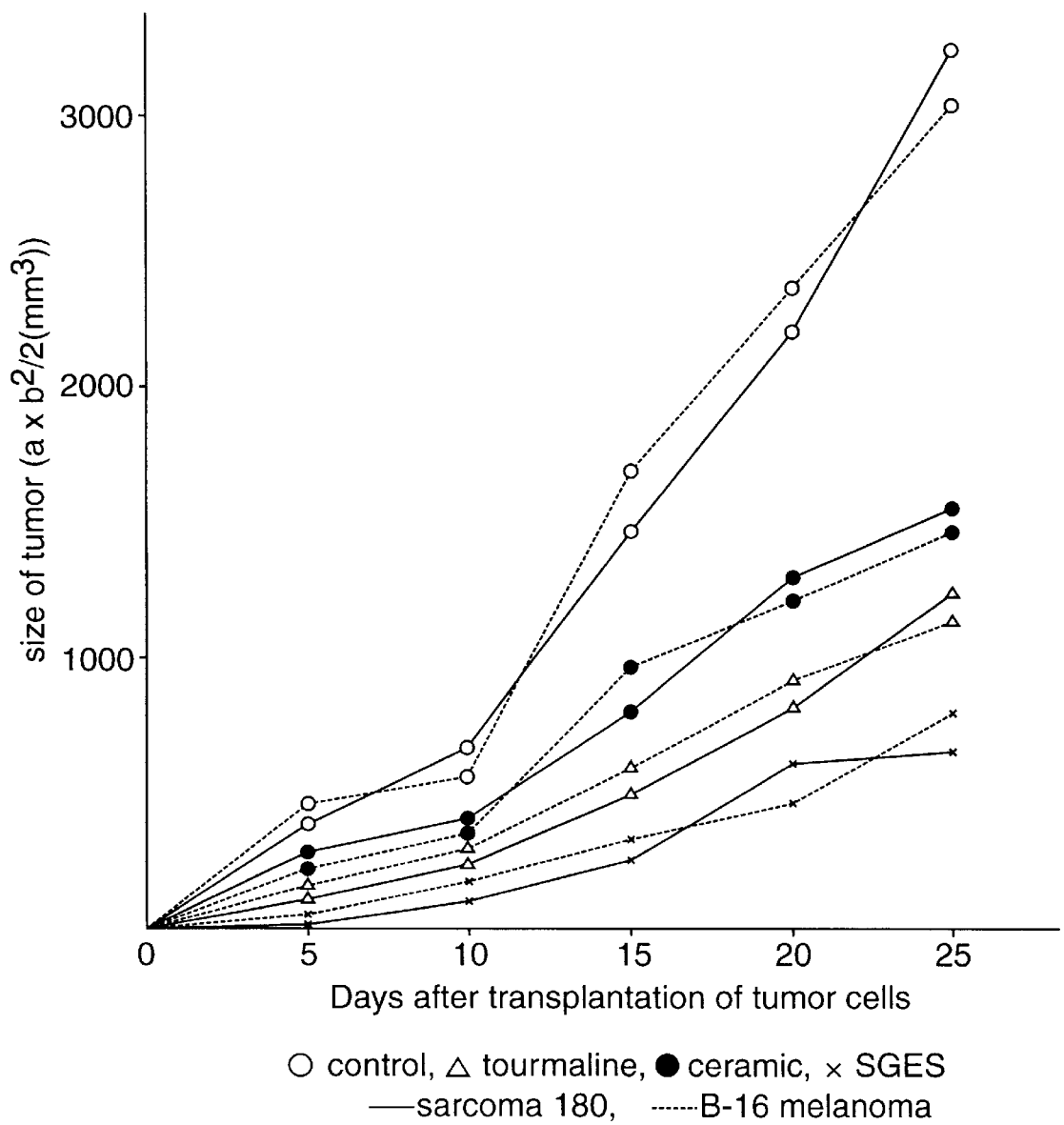
FIG. 1 is a graph showing the proliferation of tumor cells transplanted to mice whereto the far-infrared radiation is applied.

In the following, the effects of the far-infrared radiation material of the present invention will be described by referring to the examples.

EXAMPLE 1
Experiment on Human White Blood Cells

White blood cells (neutrophiles and lymphocytes) were collected from peripheral blood of healthy persons so as to be placed in a test tube, and then the far-infrared radiation emitted from SGES or from known stones was applied thereto. The effects were examined with respect to five points which are considered to be promoting factors of the activation of normal cells: (1) $Ca^{2+}$ concentration ($[Ca^{2+}]i$) in neutrophiles, (2) the migration ability of neutrophiles, (3) the englobement ability of neutrophiles, (4) the production of active oxygen ($O_2^-$) by neutrophiles, and (5) the reactivity of lymphocytes to phytohemagglutinin (PHA) (the blastogenesis).

[Experimental Method]

(1) $Ca^{2+}$ Concentration in Neutrophiles

Peripheral venous blood was collected so that neutrophiles were separated from lymphocytes by using Ficoll-Hypaque. $10^7$ cells/ml of the neutrophiles were suspended in KRP solution with 0.1 mM of $CaCl_2$, whereto 0.1 μM of Fura 2-AM was added, and the mixture was slowly shaken at 37° C. for 30 minutes. After the mixture was washed twice with KRP solution, 15 μl of $10^{-6}$ M FMLP was added thereto. The $Ca^{2+}$ concentration was measured by using a spectrophotofluorometer F-4000 (trade name, Hitachi, Ltd.).

(2) The Migration Ability of Neutrophiles

An agar plate was prepared by adding 2.5 ml of RPMI with 10% deactivated calf serum to 2.5 ml of 2.4% agar solution. Thereon three holes of the diameter 3 mm were made with the separation 8 mm along a direction from the center to the outside: in the inner hole, 10 μl of RPMI 1640 solution suspended with $10^6$ cells/ml of neutrophiles was placed; in the middle hole, 10 μl of RPMI 1640 solution only was placed as a control; and in the outer hole, 10 μl of $10^{-6}$ M fMLP was placed as a migration stimulating agent. After the agar plate was allowed to stand at 37° C. for 2 hours, the distance of the neutrophiles moved from the inner hole to the outer hole was measured, which represented the migration ability of neutrophiles.

(3) The Englobement Ability of Neutrophiles 0.1 ml of paraffin oil opsonized by human serum was added to 0.9 ml of KRP solution suspended with $2\times10^7$ cells of neutrophiles, and the mixture was allowed to stand at 37° C. for 5 minutes. After ice-cooled KRP solution was added to the mixture to stop the reaction, the surface of the neutrophiles was washed three times with KRP solution well to remove paraffin oil adhering to the surface. The paraffin oil drops englobed by the neutrophiles were extracted with a mixture of chloroform and methanol (1:2) and were measured by a spectrophotometer (absorbance: 525 nm).

(4) The Production of Active Oxygen by Neutrophiles $10^6$ cells of neutrophiles were suspended in KRP solution containing 5 mM of glucose and 1 mg/ml of gelatin, and the mixture was allowed to stand at 37° C. for 5 minutes. After 0.1 mM of ferricytochrome c and 1 mg/ml of opsonized zymozan were added threrto, the mixture was further allowed to stand at 37° C. for 5 minutes. Then 0.1 ml of the supernatant was collected, which was added to 2 ml of 100 mM $K_3PO_4$ solution (pH 7.8) with 0.1 mM of EDTA. The reduction degree of active oxygen which reduced the ferricytochrome c was measured by a spectrophotometer (absorbance: 550 nm) with two wavelengths to counter the amount of the active oxygen.

(5) The Reactivity of Lymphocytes to PHA (the blastogenesis)

$3\times10^6$ cells of lymphocytes were suspended in RPMI 1640 solution containing 20% deactivated calf serum and $2\times10^5$ cells of monocytes treated with mitomycin, whereto 10 μg/ml of PHA was added, and the mixture was allowed to stand at 37° C. for 3 days. 24 hours before the completion of the reaction, 2 Ci/mM of [$^3$H] was added to the mixture. The amount of [$^3$H] taken by the lymphocytes for the final 24 hours was measured.

[Experiment]

Ceramic balls of SGES and granite, ceramic and tourmaline, as comparative stones, were prepared by pulverizing these stones and forming the pulverized stones into spheres. After warming the ceramic balls, five kinds of the above measurement systems were covered therewith. The effects to the measured values were examined.

The experimental results are shown in Table 1.

TABLE 1

| test sample | neutrophile | | migration ability (mm) | englobement ability (OD) | $O_2^-$ prod. (nM/$10^6$ cells/min) | lymphocyte blastogenesis (PHA, cpm) |
|---|---|---|---|---|---|---|
| | [$Ca^{2+}$]i (nM) | | | | | |
| | resting | fMLP | | | | |
| granite | 79.6 ± 8.9* | 674 ± 78* | 21.2 ± 1.8* | 0.039 ± 0.004* | 1.78 ± 0.19* | 44587 ± 4904# |
| ceramic | 74.8 ± 9.2* | 661 ± 84* | 21.4 ± 1.9* | 0.038 ± 0.004* | 1.75 ± 0.21* | 45213 ± 4069# |
| tourmalin | 88.6 ± 9.2# | 726 ± 88# | 22.3 ± 2.1* | 0.042 ± 0.006* | 2.01 ± 0.18# | 47681 ± 5721$ |
| SGES | 96.5 ± 10.5# | 875 ± 95# | 24.2 ± 3.1* | 0.044 ± 0.004# | 1.90 ± 0.19# | 46994 ± 6109$ |
| control@ | 62.4 ± 7.5 | 511 ± 73 | 17.9 ± 0.9 | 0.0319 ± 0.005 | 1.48 ± 0.24 | 32671 ± 3593 |

*0.01 < p < 0.05 vs. control, # p < 0.01, ¥ p < 0.001, $ p < 0.0001.
@control: the value for a system without far-infrared radiation.

As clearly seen from Table 1, the far-infrared radiation emitted from all the ceramic balls activated normal cells. In particular, the SGES ceramic balls, the far-infrared radiation material of the present invention, were most effective for activating normal cells of the other ceramic balls.

EXAMPLE 2
Experiment on the Lipid Peroxide Production

In a thiobarbituric acid (TBA) reaction system, an oily unsaturated fatty acid, docosahexaenoic acid, reacts with active oxygen which emits ultraviolet radiation to produce lipid peroxides. To this system, the far-infrared radiation emitted from SGES or from known stones was applied. Measured was the reduction degree of lipid peroxides which are considered to be one of factors causing various diseases.

[Experimental Method]

0.1 ml of docosahexaenoic acid diluted by 200 times was prepared in order to measure lipid peroxides produced by the TBA reaction. In the TBA reaction, 0.2 ml of 7% sodium dodecyl sulfate, 2 ml of 0.1 N HCl and 0.3 ml of phosphotungstic acid were mixed, whereto 1 ml of a reagent containing 0.67% TBA and acetic acid (1:1) was added, and the measurement was performed by a spectrophotofluorometer (excitation: 515 nm and emission: 553 nm).

[Experiment]

Ceramic balls of SGES and granite, ceramic and tourmaline, as comparative stones, were prepared by pulverizing these stones and forming the pulverized stones into spheres. After warming the ceramic balls, the above measurement system was covered therewith. The effects to the measured values were examined.

The experimental results are shown in Table 2.

TABLE 2

| test sample | solvent | average (6 minutes) |
| --- | --- | --- |
| control 1 (UV−) | ethanol | 6.5 ± 0.9 |
| control 2 (UV+) | ethanol | 462 ± 61 |
| granite | ethanol | 385 ± 48* |
| ceramic | ethanol | 368 ± 41* |
| tourmaline | ethanol | 245 ± 29# |
| SGES | ethanol | 84 ± 13¥ | dil. docosahexaenoic acid (200 times) + sun light (UV) for 6 hours.
*0.01 < p < 0.05 vs. control,
p < 0.01,
¥p < 0.001.

As clearly seen from Table 2, for all the test samples, the docosahexaenoic acid with ultraviolet radiation was significantly inhibited from producing lipid peroxides (TBA reactive materials). In particular, the far-infrared radiation emitted from the SGES ceramic balls of the present invention most effectively inhibited the lipid peroxide production of those from the other ceramic balls.

EXAMPLE 3
Experiment on Leukemia Cells

Three types of leukemia cells on the market, HL-60, ML-1 and K-562, were obtained, each of which were then suspended in RPMI solution. To the system, the far-infrared radiation emitted from SGES or from known stones was applied. $Ca^{2+}$ concentration ($[Ca^{2+}]i$) in leukemia cells was measured in order to examine the degree of inhibiting the function of cancer cells.

[Experiment]

Ceramic balls of SGES and granite, ceramic and tourmaline, as comparative stones, were prepared by pulverizing these stones and forming the pulzerized stones into spheres. After warming the ceramic balls, three kinds of the above measurement systems (for HL-60, ML-1 and K-562) were covered therewith. The effects to the measured values were examined.

The experimental results are shown in Table 3.

TABLE 3

| | leukemia cell | | | | | |
| --- | --- | --- | --- | --- | --- | --- |
| | HL-60 | | ML-1 | | K-562 | |
| test | $[Ca^{2+}]i$ (nM) | | | | | |
| sample | resting | fMLP | resting | fMLP | resting | fMLP |
| granite | 60.2 ± 6.7* | 148 ± 16* | 33.6 ± 3.6 | 82.7 ± 11.4 | 21.2 ± 2.0* | 58.3 ± 5.3* |
| ceramic | 61.3 ± 3.3* | 145 ± 17* | 35.2 ± 4.2 | 84.9 ± 13.3 | 20.9 ± 1.7* | 62.1 ± 5.7* |
| tourmalin | 63.5 ± 8.0* | 159 ± 14* | 31.5 ± 4.0* | 79.3 ± 12.1* | 18.0 ± 2.1# | 47.7 ± 6.2# |
| SGES | 63.3 ± 9.5* | 169 ± 18* | 28.8 ± 3.1* | 75.8 ± 10.3* | 15.2 ± 1.9# | 40.8 ± 5.7# |
| control@ | 47.8 ± 5.6 | 128 ± 16 | 38.2 ± 4.1 | 105.6 ± 14.0 | 30.2 ± 4.4 | 87.5 ± 9.8 |

*0.01 < p < 0.05 vs. control, # p < 0.01, ¥ p < 0.001, $ p < 0.0001.
@control: the value for a system without far-infrared radiation.

It can be clearly seen from Table 3 that, except HL-60 cells, the far-infrared radiation emitted from all the ceramic balls inhibited the cancer cell function. Particularly, the SGES ceramic balls of the present invention significantly deactivated cancer cells over the other ceramic balls.

Combining those results of Examples 1 and 3, the SGES far-infrared radiation material according to the present invention powerfully activated normal cells while the same significantly deactivated cancer cells the function of which should be inhibited.

EXAMPLE 4
Experiment on Tumor Cells Transplanted to Mice

Two types of tumor cells obtained from cancer-bearing mice, sarcoma 180 and B-16 melanoma, were transplanted to the dorsum of normal ddY or C57 black mice. To the system, the far-infrared radiation emitted from SGES or from known stones was applied. The effects to the proliferation of tumor cells were examined to obtain the degree of inhibiting the proliferation of transplanted cancer cells.

[Experiment]

Sheets of cloth were prepared which comprised ceramic balls of SGES and tourmaline and ceramic, as comparative stones, obtained by pulverizing these stones and forming the pulzerized stones into spheres, and were applied onto the dorsum of two types of mice bearing sarcoma 180 and B-16 melanoma, respectively. The size of the tumor with the far-infrared radiation thereto was measured every five days so as to be compared with that without the far-infrared radiation thereto.

The experimental results are shown in FIG. 1.

As clearly seen from FIG. 1, the far-infrared radiation emitted from all the ceramic balls inhibited the proliferation of tumor cells, and controlled the proliferation of transplanted cancer cells. Especially, the SGES ceramic balls of the present invention showed the remarkable effects over the other ceramic balls.

EXAMPLE 5
Experiment on Dyshepatia Rats

Dyshepatia Wistar rats (female, 24 weeks old) by mercury poisoning were obtained by giving 6 mg/kg of mercury (HgCl$_2$) thereto. Then SGES ultrafine powder according to the present invention was administered to the rats. The effects to the amount of glutamic-oxaloacetic transaminase (GOT) and glutamic-pyruvic transaminase (GPT) in blood were examined to obtain the degree of curing dyshepatia.

[Experiment]

Ultrafine powder of SGES was prepared by pulverizing SGES and grinding the pulverized SGES. 0.006 g/kg, 0.06 g/kg and 0.3 g/kg per every day for a week of the SGES ultrafine powder each was administered to three of the above dyshepatia rats. After a week, the blood of the rats was collected so as to examine the effects to the measured values.

The experimental results are shown in Table 4.

TABLE 4

| rat group | GOT (KU) | GPT (KU) |
| --- | --- | --- |
| control | 80.3 ± 3.6 | 43 ± 0.9 |
| HgCl$_2$ (6 mg/kg) only | 132.7 ± 5.9 | 90 ± 5.5 |
| SGES (0.006 g/kg) + HgCl$_2$ (6 mg/kg) | 101.0 ± 4.2 | 49 ± 7.2 |
| SGES (0.06 g/kg) + HgCl$_2$ (6 mg/kg) | 94.8 ± 2.4 | 50 ± 2.2 |
| SGES (0.3 g/kg) + HgCl$_2$ (6 mg/kg) | 90.1 ± 5.4 | 46 ± 4.9 |
| SGES (0.006 g/kg) only | 78.8 ± 0.5 | 38 ± 1.9 |

It can be clearly seen from Table 4, the SGES ultrafine powder of the present invention remarkably reduced the amount of GOT and GPT in the blood of the dyshepatia rats, and so cured dyshepatia.

EXAMPLE 6

Clinical Test to Rheumatism Patients

To 85 cases of rheumatism patients, 0.4 g per a day of the SGES ultrafine powder of the present invention was administered, and further the rheumatism patients were covered with the SGES ceramic balls warmed at 45–46° C. for 15–20 minutes to take a sand bath. After three months, the effects were judged, whereby the results shown in Table 5 were obtained.

In Table 5, "3 points", "2 points", "1 point", "0 point" and "?" are represented as "Remarkably effective", "Effective", "Slightly effective", "No change" and "No judgment", respectively. Also CRP and E.S.R. exhibit the inflammation degree of rheumatism.

TABLE 5

| symptom | 3 pts | 2 pts | 1 pt | 0 pt | ? | total pts |
| --- | --- | --- | --- | --- | --- | --- |
| morning stiffness | 20 | 21 | 19 | 22 | 3 | 121 pts |
| arthralgia | 8 | 19 | 18 | 36 | 4 | 80 pts |
| swelling | 10 | 17 | 20 | 33 | 5 | 84 pts |
| dysfunction | 2 | 7 | 0 | 73 | 3 | 20 pts |
| CRP | 7 | 20 | 18 | 35 | 5 | 79 pts |
| E.S.R. | 8 | 15 | 14 | 42 | 6 | 68 pts |

The reduction degree of lipid peroxides in blood of the rheumatism patients of the above-mentioned 85 cases was also examined, the results after three months of which were shown in Table 6.

TABLE 6

| no change | 8 cases |
| --- | --- |
| 0–20% reduction | 6 cases |
| 21–40% reduction | 24 cases |
| 41–60% reduction | 43 cases |

TABLE 6-continued

| 61–80% reduction | 4 cases |
| --- | --- |
| 81–90% reduction | 0 cases |
| total | 85 cases |

As clearly seen from Table 5, the combined treatment of administering the SGES ultrafine powder together with taking the SGES sand bath of the present invention was effective to rheumatism patients, and more particularly to a symptom of morning stiffness and also of arthralgia. Also CRP was improved by this combined treatment.

Furthermore, from Table 6, most of rheumatism patients showed the reduction of lipid peroxides in blood while only 8 out of 85 cases, less than 10%, of rheumatism patients did not. Both the above results showed the remarkable effectiveness of the combined treatment of administering the SGES ultrafine powder and taking the SGES sand bath of the present invention to rheumatism patients.

Although illustrative examples of the present invention have been shown and described, a latitude of modification, change and substitution is intended in the foregoing disclosure, and in certain instances, some features of the present invention will be employed without a corresponding use of other features. Accordingly, it is appropriate that the appended claims be construed broadly and in a manner consistent with the scope of the present invention.

The followings are the effects obtained by the present invention.

As seen from the result of Example 1, the far-infrared radiation emitted from the SGES ceramic balls according to the present invention activates normal cells more effectively than from any other known ceramic balls.

From the results of Examples 2, 3 and 4, the far-infrared radiation from the SGES ceramic balls according to the present invention significantly inhibits such factors which cause various diseases as the lipid peroxide production and the proliferation of leukemia and cancer cells over any other known ceramic balls.

Furthermore, from the results of Example 5 and 6, the SGES ultrafine powder according to the present invention cures dyshepatia, and the combination of administering the SGES ultrafine powder and taking the SGES sand bath is effective to rheumatism, and more specifically to such symptoms of rheumatism as morning stiffness, arthralgia, swelling, and so on.

Since the combination of administering the SGES ultrafine powder and taking the SGES sand bath also reduces lipid peroxides in blood, it can be used as a medicine for curing such diseases which is considered to be caused by lipid peroxides as rheumatoid arthritis, thrombophlebitis, progressive systemic scleroderma, Buerger's disease, Raynaud's disease, intractable dermatoulcer, and the like.

The SGES ultrafine powder is free from side effects, and threrfore can be taken as a health food for maintaining and promoting a person's health.

What is claimed is:

1. A far-infrared radiation material obtained by the following steps:

pulverizing a stone being mined from the Sobo Mountains in Oita, Japan, which stone emits far-infrared radiation having a wavelength of between 4 to 14 mu.m. (micrometers), which stone includes at least the following four elements: Sl, AL, K and Fe, each element being present in the amount of at least approximately 28%, 10%, 6% and 4% respectively in said stone; and sintering the pulverized stone to form each pulverized stone into a more spherical shape.

2. The material prepared according to the method of claim 1, wherein the stones having an equivalent spherical diameter of 3 to 5 millimeters.

3. The material prepared according to the method of claim 1, wherein said sintering is carried out at a temperature in the range of 1100° C. to 1150° C.

4. The method according to claim 1, wherein said sintering is carried out a temperature above 1000° C. for 15 to 25 hours.

* * * * *

UNITED STATES PATENT AND TRADEMARK OFFICE
CERTIFICATE OF CORRECTION

PATENT NO. : 6,004,588
DATED : December 21, 1999
INVENTOR(S) : Kazuyuki Torii and Kozo Niwa It is certified that error appears in the above-indentified patent and that said Letters Patent is hereby corrected as shown below:

In Column 1, line 42: delete "a topic" and insert "atopic".

In Column 1, line 56: delete "SOES" and insert "SGES".

In Column 9, line 6, (Claim 1): insert "pulverized" prior to the word "stones".

Signed and Sealed this

Eighth Day of August, 2000

Attest:

Q. TODD DICKINSON

Attesting Officer

Director of Patents and Trademarks